(12) United States Patent
Williams

(10) Patent No.: US 9,107,839 B1
(45) Date of Patent: Aug. 18, 2015

(54) HAIR CARE COMPOSITION

(71) Applicant: Gwendolyn J. Williams, Canton, MI (US)

(72) Inventor: Gwendolyn J. Williams, Canton, MI (US)

(73) Assignee: Gwendolyn J. Williams, Canton, MI (US)

( * ) Notice: Subject to any disclaimer, the term of this patent is extended or adjusted under 35 U.S.C. 154(b) by 0 days.

(21) Appl. No.: 14/273,011

(22) Filed: May 8, 2014

(51) Int. Cl.
| | |
|---|---|
| *C11D 7/02* | (2006.01) |
| *C11D 7/24* | (2006.01) |
| *C11D 7/26* | (2006.01) |
| *A61K 8/25* | (2006.01) |
| *A61Q 5/02* | (2006.01) |
| *A61K 8/92* | (2006.01) |
| *A61K 8/34* | (2006.01) |
| *C11D 3/12* | (2006.01) |
| *C11D 3/20* | (2006.01) |
| *C11D 3/382* | (2006.01) |

(52) U.S. Cl.
CPC . *A61K 8/25* (2013.01); *A61K 8/345* (2013.01); *A61K 8/922* (2013.01); *A61Q 5/02* (2013.01); *C11D 3/128* (2013.01); *C11D 3/1253* (2013.01); *C11D 3/1266* (2013.01); *C11D 3/2034* (2013.01); *C11D 3/2065* (2013.01); *C11D 3/382* (2013.01)

(58) Field of Classification Search
CPC .... C11D 3/1266; C11D 3/1253; C11D 3/128; C11D 3/2034; C11D 3/2065; C11D 3/382; A61Q 5/02

USPC ......... 510/119, 130, 136, 137, 138, 462, 463, 510/505, 506, 507
See application file for complete search history.

(56) References Cited

U.S. PATENT DOCUMENTS

| | | | | |
|---|---|---|---|---|
| 5,366,665 | A * | 11/1994 | Cho | 510/152 |
| 2004/0170590 | A1* | 9/2004 | Fahnestock et al. | 424/70.14 |
| 2005/0008604 | A1* | 1/2005 | Schultz et al. | 424/70.14 |
| 2006/0223728 | A1* | 10/2006 | Tokunaga | 510/124 |
| 2007/0031365 | A1* | 2/2007 | Terada | 424/70.122 |
| 2010/0040654 | A1* | 2/2010 | Wake et al. | 424/401 |
| 2012/0065115 | A1* | 3/2012 | Johnson | 510/121 |
| 2013/0287708 | A1* | 10/2013 | Silberstein et al. | 424/49 |
| 2014/0086864 | A1* | 3/2014 | Ishimori et al. | 424/70.122 |

FOREIGN PATENT DOCUMENTS

WO    WO2012/077120    *    6/2012

OTHER PUBLICATIONS

Shakara Natural Tips, "What is Rhassoul Clay?", p. 1-5, Feb. 16, 2012.*
Longing4Length—Growing Long Hair the Healthy Way, "Clays for Hair: Benefits & Types", p. 1-5, May 6, 2013.*
Argana Vita, "Rhassoul Clay", p. 1-3, 2012.*

* cited by examiner

*Primary Examiner* — Gregory R Delcotto

(57) ABSTRACT

The present invention relates a hair care composition; the composition comprises a shampoo or cleansing agent derived from Rhassoul clay mixed with water, a conditioning agent and a detangling agent derived from naturally occurring plant material, and a preservative.

3 Claims, 1 Drawing Sheet

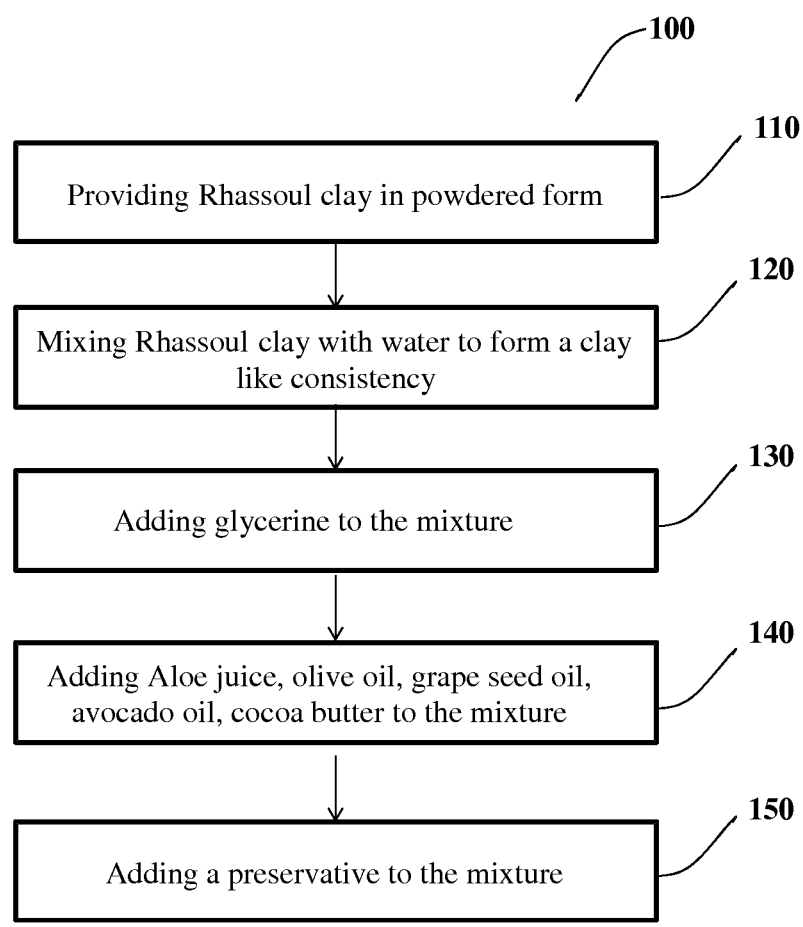

HAIR CARE COMPOSITION

FIELD OF THE INVENTION

The present invention relates to compositions for a hair care product and, in particular, to a multi-benefit hair care product that acts as a shampoo or a cleanser, detangler, smoothing conditioner, deep conditioner and leave-in conditioner.

BACKGROUND OF THE INVENTION

Human hair becomes soiled due to its contact with the surrounding atmosphere and, to a greater extent, from sebum secreted by the head. The soiling of the hair necessitates it being shampooed with frequent regularity. However, the shampooing process has disadvantages in that the hair is left in a wet, tangled and generally unmanageable state. After shampooing, the hair can also suffer from a loss of luster due to removal of natural oils or other hair moisturizing materials. A variety of approaches have been developed to alleviate the after-shampoo problems ranging from the inclusion of hair conditioning aids in shampoo to post-shampoo application of hair conditioners, which are generally liquid in nature and must be applied in a separate step following the shampooing, left on the hair for a length of time, and rinsed with fresh water.

Hair conditioners have often been separate from the shampoo. However, the desire by the consumer for the convenience of personal hair care products having both cleaning and conditioning functions in the same product has increased. Such products are known as 2-in-1 conditioning shampoos. These contain both cleaning and conditioning surfactants. Such conditioning shampoos clean soiled hair and leave a conditioner in the hair at the same time. Thus, it is unnecessary for the consumer to subsequently use a conditioner after using the shampoo. In addition to cleansing and conditioning, there also exists a need for detangling, exfoliation, and detoxification in order to provide adequate care for hair.

Conventional surfactants are designed to be extremely effective emulsifiers, stripping the skin and scalp bare of its natural oils and emollients. This however, results in irritation, dry skin and inflammation, opening it up to loss of hair, dandruff and itching and flaking. Much interest in natural cleansers has developed in the consumer, and numerous cleansing agents described as natural are being marketed to the public to take advantage of this interest.

Rhassoul or Ghassoul clay is a naturally occurring powder-like substance found in the Atlas Mountains of Morocco. Rhassoul occurs in the form of a brown rock composed of more than 90% of a mineral called stevensite Li-rich (montmorillonite clay) and also comprises silica, iron, magnesium, potassium, sodium, lithium and trace elements. Rhassoul clay is also known as Moroccan lava clay which can be mixed with water and used as a natural cleansing agent for skin and hair care.

Conditioning shampoo compositions and multi-purpose hair care products are disclosed in a number of publications. U.S. Pat. No. 5,939,059 discloses a 2-in-1 hair conditioning shampoo composition. PCT publication WO1992005764 A1 shows an improved shampoo composition comprising hair conditioners, antidandruff agents, anti-lice agents, styling agents and its mixtures. U.S. Patent publication US20060286062 A1 discloses natural shampoo and body wash composition derived from plants and natural clays. PCT publication WO2010137930 A2 shows a hair care product derived from a mixture of Rhassoul clay, natural essential oils and plant extracts.

Moreover, conventional cleansing conditioners and shampoos generally employ chemical agents as surfactants, which results in dryness of hair and excessive removal of natural oil from the scalp, leaving it prone to infections like dandruff. Furthermore, procuring and usage of separate hair care products for cleansing, conditioning, exfoliating and detoxifying proves to be cumbersome and expensive. Further limitations of the prior art conditioning shampoo compositions includes dryness-induced frizz and tangled hair, leading to hair breakage and eventually hair loss.

For instance, it remains desirable to improve overall conditioning, and especially shine and luster, wet and dry combing, and feel of the hair after being treated with shampoo. However merely increasing the level of one or both conditioning ingredients can result in adverse effects such as the hair feeling greasy, as well as loss of fullness and volume. It is desirable to improve conditioning without suffering from these drawbacks.

In spite of all these approaches and attempts to provide optimum combinations of shampoos and hair conditioners, it remains desirable to provide still improved conditioning shampoos made from naturally occurring products for complete hair care including cleansing, conditioning and detangling.

SUMMARY OF THE INVENTION

The present invention discloses a hair care composition comprising: a shampoo or cleansing agent comprising naturally occurring Rhassoul clay combined with water; a conditioning agent and a detangling agent, wherein the conditioning agent and detangling agent are derived from a plant material; and a preservative for preventing microbial growth.

In one embodiment of the present invention, the conditioning agent of the hair care composition comprises a smoothing conditioner, a deep conditioner and a leave-in conditioner selected from a group comprising Aloe vera leaf extract, cocoa seed butter, olive fruit oil, grape seed oil, avocado oil, and its combinations thereof.

A further embodiment of the present invention provides a method of preparing a multi-benefit hair care composition, the method comprising: mixing Rhassoul clay with water to form a mixture with clay-like consistency; adding glycerine to the mixture; adding aloe vera leaf extract, olive oil, avocado oil, grape seed oil and cocoa seed butter to the mixture; and finally adding a preservative to the mixture.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the detailed description is to be regarded as illustrative in nature and not as restrictive.

BRIEF DESCRIPTION OF DRAWINGS

FIG. 1 shows a flowchart for a method of preparing a multi-benefit hair care composition according to an embodiment of the present invention.

DETAILED DESCRIPTION OF THE INVENTION

The hair care composition or shampoo compositions of the present invention can comprise, consist of, or consist essentially of the essential elements and limitations of the invention described herein, as well any of the additional or optional ingredients, components, or limitations described herein.

According to the present invention, the composition for hair care comprises a cleansing agent or shampoo comprising Rhassoul clay combined with water as the main ingredient, along with additional ingredients such as a conditioning agent, a detangling agent and a preservative. Rhassoul clay is a naturally occurring powder-like substance from the Atlas Mountains of Morocco, Africa. It is rich in silica, iron, magnesium, potassium, sodium, lithium and trace elements and possesses significant cleansing property.

The Rhassoul clay also known as Ghassoul or Moroccan lava clay generally occurs in powder form, and can also be used in other forms and consistency such as in viscous, colloidal, creamy, flowing gel, blades, chips and powder form. Rhassoul clay is mixed with water to achieve clay-like consistency and acts as an efficient cleansing agent which removes excess oil, dirt, toxins, and also exerts exfoliating effect on the scalp.

In one embodiment of the present invention, the conditioning agent includes or performs the function of different types of conditioners such as a smoothing conditioner, a deep conditioner and a leave-in conditioner. The conditioning agent is obtained from a naturally occurring plant material and, hence, free from synthetic chemical agents like sulphate, paraben, phthalate, gluten and the like thereof.

The conditioning agent is selected from a group comprising Aloe vera leaf extract, Cocoa seed butter, olive fruit oil, grape seed oil, avocado oil, and its combinations thereof. Similarly, the detangling agent of the hair care composition comprises of glycerine. In an embodiment, the detangling agent comprises vegetable glycerine.

In an embodiment, the conditioning agent is selected from a group comprising *Aloe barbadensis* leaf extract, *Theobroma cacao* seed butter, *Olea europaea* fruit oil, *Vitis vinfera* seed oil and *Persea gratissima* oil.

A preservative compound is needed for retaining the freshness of the composition and to avoid invasion by bacterial growth and mildew formation. In an embodiment, phenoxyethanol is added as a preservative. In some cases, certain natural preservatives can also be added to the hair care composition in order to render it as an organic hair care product.

In another embodiment, the hair care composition further comprises compounds such as anti-dandruff agents, anti-lice agents, styling agents and coloring agents for additional benefits thereby making the composition as a multi-purpose hair care product.

The hair care composition of the present invention results in a 5-in-1 product that performs the function of a detoxifying cleanser, a smoothing conditioner, a detangler, a deep conditioner and a leave-in conditioner. The conditioning agent selected from olive fruit oil, cocoa seed butter and aloe vera juice retains natural luster and softness of the hair after shampooing.

The composition of individual compounds can be altered suiting different hair types and hair textures, thus catering to a broad range of customers. For example, curly and wavy hair textures require different conditioning treatments compared to straight hair textures or coily hair textures.

In a further embodiment, FIG. 1 shows a flow chart for a method of preparing a multi-benefit hair care composition 100, the method 100 comprising: providing Rhassoul clay in powdered form as shown in 110; mixing Rhassoul clay with water to form a mixture with clay like consistency as shown in 120; adding glycerine to the mixture as shown in 130; adding aloe vera leaf extract, olive oil, grape seed oil, avocado oil and cocoa seed butter to the mixture as shown in 140; and adding a preservative to the mixture as shown in 150.

The hair care composition of the present invention may further comprise one or more optional components known for use in shampoo or conditioning compositions, provided that the optional components are physically and chemically compatible with the essential component described herein, or do not otherwise unduly impair product stability, aesthetics or performance.

Optional components include anti-static agents, dyes, organic solvents or diluents, pearlescent aids, foam boosters, additional surfactants or co-surfactants (nonionic, cationic, zwitterionic), pediculocides, pH adjusting agents, perfumes, preservatives, proteins, skin active agents, suspending agents, styling polymers, sunscreens, thickeners, vitamins, and viscosity adjusting agents. This list of optional components is not meant to be exclusive, and other optional components can be used.

A method for cleansing and conditioning the hair comprises the steps of: a) wetting the hair thoroughly with water, b) applying an effective amount of the hair care composition to the hair, preferably from root to tip c) gently massaging hair and scalp d) gently detangling, followed by rinsing the product from hair using water. These steps can be repeated as many times as desired to achieve the desired cleansing and conditioning benefit.

The hair care composition or shampoo compositions of the present invention can be prepared by using various formulation and mixing techniques or methods known in the art for preparing shampoo or conditioning compositions, or other similar compositions.

In an embodiment, the hair care composition comprises in percent by weight, Rhassoul clay in the range of 30 to 35 percent mixed with 40 to 45 percent water, detangling agent in range of 3 to 6 percent, conditioning agents in the range of 0.5 to 8 percent and preservative in the range of 4 to 8 percent.

EXAMPLE

Example 1

The hair care composition of the present invention comprises the following ingredients in referred quantity according to an exemplary embodiment.

| Ingredients | In percent (by weight) |
| --- | --- |
| 1. Rhassoul clay | 33 |
| 2. Water | 42 |
| 3. Cocoa Butter | 5.2 |
| 4. Glycerine | 4.9 |
| 5. Aloe juice | 4.2 |
| 6. Olive oil | 1.33 |
| 7. Avocado oil | 1.33 |
| 8. Grapeseed oil | 1.33 |
| 9. Phenoxyethanol | 6.7 |

What is claimed is:

1. A multi-benefit hair care composition, comprising:
Rhassoul clay in a range of 30-35% by weight, combined with water in a range of 40-45% by weight;

a conditioning agent in a range 0.5-13.4% by weight, comprising cocoa seed butter, *Aloe vera* leaf extract, olive fruit oil, avocado oil and grape seed oil;

a detangling agent comprising glycerine in a range of 3-6% by weight; and a preservative comprising phenoxyethanol in a range of 4-8% by weight.

2. The composition of claim 1, wherein the conditioning agent functions a smoothing conditioner, a deep conditioner and a leave-in conditioner.

3. The composition of claim 1, wherein the conditioning agent comprises by weight, 4.2% *Aloe vera* leaf extract, 5.2% Cocoa seed butter, 1.33% olive fruit oil, 1.33% grape seed oil and 1.33% avocado oil.

\* \* \* \* \*